United States Patent [19]
Kastner et al.

[11] 4,309,504
[45] Jan. 5, 1982

[54] PROCESS FOR PREPARING NARASIN

[75] Inventors: Ralph E. Kastner, Indianapolis; Robert L. Hamill, Greenwood, both of Ind.

[73] Assignee: Eli Lilly and Company, Indianapolis, Ind.

[21] Appl. No.: 115,656

[22] Filed: Jan. 28, 1980

[51] Int. Cl.$^3$ ............................................. C12P 17/16
[52] U.S. Cl. .................................. 435/118; 435/253; 435/886
[58] Field of Search ................................. 435/119, 118

[56] References Cited

U.S. PATENT DOCUMENTS 4,038,384  7/1977  Berg et al. ............................ 435/118

OTHER PUBLICATIONS

DeBoer et al., Antibiotics Annual, 1955-1956, pp. 886-892.
Berg et al., Journal of Antibiotics, vol. 31, pp. 1-6, 1978.
Boeck et al., Development in Industrial Microbiology, vol. 18, pp. 471-485, (1977).

*Primary Examiner*—Alvin E. Tanenholtz
*Attorney, Agent, or Firm*—Dwight E. Morrison; Arthur R. Whale

[57] ABSTRACT

The new microorganism *Streptomyces lydicus* DeBoer et al., NRRL 12034 and the fermentation process for preparing narasin by submerged aerobic fermentation of this organism.

4 Claims, No Drawings

PROCESS FOR PREPARING NARASIN

BACKGROUND OF THE INVENTION

1. Field of the Invention

This invention relates to a new microbiological process for preparation of the antibiotic narasin, which antibiotic is active as an antibacterial agent, an anticoccidial agent, and as an agent for increasing ruminant feed-utilization efficiency.

2. Description of the Prior Art

Narasin is a known polyether antibiotic. Production of narasin by fermentation of *Streptomyces aureofaciens* NRRL 5758 or *Streptomyces aureofaciens* NRRL 8092, has been described by Berg et al., U.S. Pat. No. 4,038,384 (July 26, 1977). See also Berg et al. in the *Journal of Antibiotics*, 31, 1–6 (1978).

Boeck et al. describe "Narasin, A New Polyether Antibiotic: Discovery and Fermentation Studies," Chapter 38, Pages 471–485, Volume 18, Development In Industrial Microbiology [A Publication of the Society for Industrial Microbiology (1977)].

Narasin is active against gram-positive bacteria, anaerobic bacteria, and fungi, and is useful as an anticoccidial agent and as an agent for increasing feed-utilization in ruminants.

SUMMARY OF THE INVENTION

The present invention relates to a new process for the preparation of the antibiotic narasin by cultivating a newly discovered strain designated herein as *Streptomyces lydicus* DeBoer et al., NRRL 12034, or a narasin-producing mutant or variant thereof, in a culture medium containing assimilable sources of carbon, nitrogen, and inorganic salts under submerged aerobic fermentation conditions until a substantial amount of narasin is produced by said organism in said culture medium and, optionally, isolating said narasin from the culture medium.

This invention further relates to the biologically pure culture of the microorganism *Streptomyces lydicus* DeBoer et al., NRRL 12034, which is useful for the production of narasin.

DETAILED DESCRIPTION

The new microorganism of this invention, useful for producing the antibiotic narasin, is a biologically pure culture derived from a soil sample collected near the Surinam River, Surinam, South America, and the culture was given the number A-39861.3 for identification purposes.

Culture A-39861.3 is classified as a strain of *Streptomyces lydicus* DeBoer et al., based upon a simultaneous culturing of *Streptomyces hygroscopicus; Streptomyces endus; Streptomyces platensis;* and *Streptomyces lydicus* using the methods and media recommended by Shirling and Gottlieb ["Methods of Characterization of Streptomyces species," *Intern. Bull. of Systematic Bacteriol.* 16, 313–340 (1966)], along with certain supplementary tests. From the characteristics obtained, *Streptomyces lydicus* was selected as being the most closely related species. The principal differences between culture A-39861.3 and the *S. lydicus* type culture are in the carbon utilization pattern, a higher level of NaCl tolerance by *S. lydicus*, and the production of a white aerial mycelium by culture A-39861.3 on several media.

Color names were assigned according to the ISCC-NBS method (K. L. Kelly and D. B. Judd, "The ISCC-NBS Methods of Designating Colors and a Dictionary of Color Names," U.S. Department of Commerce Circ. 553, 1955, Washington, D.C.). Figures in parentheses refer to the Tresner and Backus color series [H. D. Tresner and E. J. Backus, "System of Color Wheels for Streptomycete Taxonomy," *Appl. Microbiol.* 11, 335–338 (1956)]. Color tab designations are underlined. The Maerz and Paul color blocks (A. Maerz and M. R. Paul, "Dictionary of Color," McGraw-Hill Book Co., Inc., New York, N.Y., (1950) are enclosed in brackets.

The cell-wall sugars were determined using a modification of the procedure of M. P. Lechavalier ["Chemical Methods as Criteria for the Separation of Actinomycetes Into Genera." Workshop sponsored by the Subcommittee on Actinomycetes of the American Society of Microbiology. Dr. Thomas G. Pridham, Convenor. Held at the Institute of Microbiology, Rutgers University, The State University of New Jersey, New Brunswick, N.J., (1971)]. The isomers of diaminopimelic acid were determined using the method of Becker et al., *Appl. Microbiol.* 11, 421–423 (1964). All plates were read after 13 days at 30° C., unless otherwise noted.

CHARACTERIZATION OF NARASIN-PRODUCING STRAIN

Morphology

Spores are smooth as determined by electron microscopy. The sporophores are spiralled with the spirals being open and not tightly coiled. Spirals of 2–3 turns are common. An occasional hook or loop is observed. Spores are oval to slightly cylindrical and measure an average of 1.365 $\mu$m × 1.69 $\mu$m with a range of 1.3 $\mu$m to 1.95 $\mu$m × 1.3 $\mu$m to 2.6 $\mu$m.

TABLE I

Cultural Characteristics on Various Media

| Medium | Characteristics |
|---|---|
| Tomato paste oatmeal agar | Abundant growth, reverse medium yellow-brown [14F6] to black [8C8] toward center of inoculum. Aerial mycelium abundant. Gray (GY) 3fe light brownish-gray to 4ig light grayish-brown. No soluble pigment. Hygroscopic |
| Yeast extract malt extract agar (ISP medium #2) | Abundant growth, reverse light brown [13F8]. Good aerial mycelium. White (W) b white; no soluble pigment. |
| Oatmeal agar (ISP medium #3) | Abundant growth, reverse light-grayish olive [13H4]. Abundant aerial mycelium (GY) 3fe light brownish-gray. Greenish soluble pigment. Black hygroscopic areas by border of inoculum. |
| Inorganic salts starch agar (ISP medium #4) | Abundant growth, reverse in younger growth brown to yellow-brown (7 days) becoming dark gray [8A9] to black [8A8] by 14 days. Good aerial (GY) d light gray. Hygroscopic. |
| Glycerol asparagine agar (ISP medium #5) | Abundant growth, reverse medium yellow-brown [14J7]. Good aerial mycelium and spores (W) b white. Slight brown soluble pigment. |
| Emerson's agar | Abundant growth, reverse strong yellow-brown [. Abundant aerial mycelium and spores (W) b white. No soluble pigment. |
| Bennett's modified agar | Good growth, reverse brownish-orange [12B9]; scant or no aerial mycelium; when present (GY) 2dc yellowish-gray. No soluble |

TABLE I-continued

| Medium | Cultural Characteristics on Various Media |
|---|---|
| | Characteristics |
| | pigment. |
| Czapek's solution agar | Growth scant as well as no aerial mycelium or spores. No color assignment. |
| Nutrient agar | Good growth, reverse pale yellow [11C2]. No aerial mycelium or spores; no soluble pigment. |
| Calcium malate agar | Good growth, reverse light grayish-olive [14B2]; no aerial mycelium or spores. Slight brown soluble pigment. |
| Glycerol-glycine agar | Good growth, reverse moderate olive [15L6]. Good aerial mycelium and spores (GY) 2dc yellowish-gray. No soluble pigment. |
| Tryptone yeast extract agar | Scant growth as well as no aerial mycelium or spores. No color assignments. |
| Tyrosine agar | Good growth, reverse light yellowish-brown [13H7]. Good aerial mycelium and spores (Y) 2db to 2fb pale yellow. Slight brown soluble pigment. |
| Glucose asparagine agar | Good growth, reverse light yellowish-brown [13H7]. Good aerial mycelium and spores (GY) 2dc yellowish-gray. No soluble pigment. |

The organism was studied for selected physiological properties in accordance with standard procedures. The properties observed and characteristics found are recorded in Table II:

TABLE II

PHYSIOLOGICAL PROPERTIES OF A-39861.3

| Production of Melanoid-Like Pigment on: | |
|---|---|
| 1. Peptone yeast extract iron slants | No melanoid pigment |
| 2. Tyrosine agar slants | No melanoid pigment |
| 3. Tryptone yeast extract broth | No melanoid pigment |
| Nitrate reduction | Positive |
| Gelatin liquefaction | Gelatin 60% liquefied by 14 days. |
| Potato plug | Good yellow-brown vegetative growth. No aerial mycelium; color of potato plug not changed. |
| Carrot plug | No growth |
| Starch hydrolysis | Starch hydrolyzed |
| Skim milk | Milk peptonized |
| Temperature Requirements | |
| Use ISP #2 agar, yeast extract-malt extract agar slants. Incubate slants at 20°, 25°, 30°, 37°, 43°, and 49° C. | No growth at 20° or 49° C. Optimum growth 25°-37° C. Some growth at 43° C. |
| NaCl Tolerance | |
| Use ISP #2 agar, yeast extract Malt extract agar add NaCl at levels of 1%, 2%, 3%, 4%, 5%, 6%, 8%, 10%, and 12%. ISP #2 agar without added NaCl served as control. | Tolerates levels of 1% to 3%; at levels >3% no growth was observed. |
| Reaction to Changes in pH | |
| Use ISP #2, agar, yeast extract-malt extract agar. Adjust pH of agar to levels of 5.0, 6.0, 7.0, 8.0, 10.0, and 11.5 after autoclaving for sterilization. | Abundant growth and sporulation from pH 5.0 to pH 8.0. At pH 10.0 growth was as isolated colonies with scant aerial mycelium. At pH 11.5, no growth. |

Carbon utilization was determined using Pridham and Gottlieb's basal medium to which the carbon sources were added at a final concentration of 1.0%, according to the teaching of Shirling and Gottlieb, supra. The carbon sources were sterilized before being added to the basal medium. Plates were read after five, nine, and sixteen days incubation at 30° C., the final readings being reported.

The results of the carbon utilization tests carried out with culture A-39861.3 are set forth in Table III.

TABLE III

CARBON UTILIZATION

| Substrate: Carbon Sources Added to Pridham and Gottlieb's Basal Medium | Reaction of A-39861.3 at 16 Days |
|---|---|
| D-Glucose* | ++ |
| D-Xylose* | + |
| L-Arabinose* | ++ |
| L-Rhamnose* | ++ |
| D-Fructose* | ++ |
| D-Galactose | ++ |
| Raffinose* | − |
| D-Mannitol* | − |
| i-Inositol* | + |
| Salicin | + |
| Sucrose* | ± |
| Cellobiose | ++ |
| D-Maltose | ++ |
| Melibiose | − |
| Melezitose | ± |
| Soluble Starch | ++ |
| Trehalose | ++ |
| Turanose | ± |

*Carbon Sources of the International Streptomyces Project (Shirling and Gottlieb, supra.
Key:
++ = Strong positive utilization
+ = Positive utilization
± = Doubtful utilization
− = Negative utilization

Cell Wall Studies

Using hydrolyzed whole cells of the organism, the presence of certain diagnostic sugars were determined. Isolated cell walls were used to determine the isomers of diaminopimelic acid. The results of these cell-wall studies are set forth below.

| Test | Result Observed |
|---|---|
| Isomers of diaminopimelic acid | LL-isomer |
| Diagnostic sugars detected | Glucose, Ribose |

A comparison of the carbon utilization pattern of strain A-39861.3 and *Streptomyces lydicus* is set forth in Table IV, which follows.

TABLE IV
CARBON UTILIZATION PATTERN OF A-39861.3 AND STREPTOMYCES LYDICUS

| Carbon Source | A-39861.3 | S. lydicus |
|---|---|---|
| D-Glucose | ++ | ++ |
| L-Arabinose | ++ | ++ |
| D-Xylose | ++ | + |
| i-Inositol | ++ | ++ |
| D-Mannitol | − | ++ |
| L-Rhamnose | ++ | − |
| Raffinose | − | ++ |
| D-Mannitol | − | ++ |
| Salicin | + | + |
| Sucrose | ± | ++ |
| Cellobiose | ++ | ± |
| D-Maltose | ++ | ++ |
| Melizitose | ± | ++ |
| Soluble Starch | ++ | ++ |
| Trehalose | ++ | ++ |

++ = Strong positive utilization
+ = Positive utilization
± = Doubtful utilization
− = Negative utilization Similarities and differences between A-39861.3 and *Streptomyces lydicus* are outlined in Table V.

TABLE V
SIMILARITIES AND DIFFERENCES BETWEEN A-39861.3 and S. lydicus

| Test, Characteristic, etc. | A-39861.3 | S. lydicus |
|---|---|---|
| Sporophores morphology | Spiralled | Spiralled |
| Spore ornamentation | Smooth | Smooth |
| Melanoid pigment | Negative | Negative |
| *Aerial mycelium | Principally gray-white on some media | Gray |
| Gelatin liquefaction | + | + |
| *Skim milk | Peptonized | Hydrolyzed |
| *Nitrate reduction | + | − |
| *NaCl tolerance | 3% | 8% |
| Isomer of diaminopimelic acid | LL-isomer | LL-isomer |

*Denotes differences.

The morphological and physiological properties of these two strains are in good agreement except for the nitrate reduction differences shown in Table V. The other closely related species differ from culture A-39861.3 as follows:

1. *Streptomyces hygroscopicus* and *Streptomyces endus* produce warty spores, whereas the spore ornamentation of culture A-39861.3 is smooth.
2. *Streptomyces platensis* differs from A-39861.3 by producing an orange-brown to red-brown vegetative mycelium on some media. Also, *Streptomyces hygroscopicus*, *Streptomyces endus*, and *Streptomyces platensis* are extremely hygroscopic, whereas, the hygroscopic characteristic of *Streptomyces lydicus* is not as pronounced.

The narasin-producing *Streptomyces lydicus* DeBoer et al., organism has been deposited and made a part of the stock culture collection of the Northern Regional Research Center, U.S. Department of Agriculture, Agricultural Research Service, Peoria, Illinois, 61604, from which it is available to the public under the number NRRL 12034.

As is the case with other organisms, the characteristics of the narasin-producing culture *Streptomyces lydicus* DeBoer et al., NRRL 12034, are subject to variation. For example, mutants (spontaneous or induced), transconjugants and recombinants (including recombinant DNA on plasmids) of the NRRL 12034 strain, or derived from this strain, which produce the narasin antibiotic may be used in this invention.

A number of different media may be used to produce narasin with *Streptomyces lydicus* DeBoer et al., NRRL 12034. These media should contain assimilable sources of carbon, nitrogen, and inorganic salts. Suitable carbon sources include glucose, starch, and dextrin. Suitable nitrogen sources include peptone, enzyme-hydrolyzed casein, cottonseed meal, and meat peptone.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

It may be necessary to add small amounts (i.e., 0.2 ml/L.) of an antifoam agent such as propyleneglycol to large-scale fermentation media if foaming becomes a problem.

For producing substantial quantities of narasin employing NRRL 12034, submerged aerobic fermentation in tanks is utilized. However, small amounts of narasin may be obtained by shake-flask culture. For tank fermentation, it is preferable to use a vegetative inoculum. The vegetative inoculum is prepared by inoculating a small volume of culture medium with the spore form, mycelial fragments, or a lyophylized pellet of the organism to obtain a fresh, actively growing culture of the organim. The vegetative inoculum is then transferred to a larger tank where, after a suitable incubation time, the narasin antibiotic is produced in optimal yield.

The pH of the uninoculated fermentation medium varies with the medium used for production, but the pH of all of the fermentation media falls in the range of from about pH 6.5 to about 7.5.

This narasin-producing organism can be grown over a broad temperature range of from about 25° to about 37° C. Optimum production of narasin with NRRL 12034 appears to occur at a temperature of about 30° C.

As is customary in aerobic submerged culture processes, sterile air is dispersed through the culture medium. For efficient growth of the organism, the volume of the air used in tank production is in the range of from about 0.25 to about 1.0 volume of air per volume of culture medium per minute (v/v/m). An optimum rate in a 10-liter vessel is about 0.5 v/v/m with agitation provided by conventional impellers rotating at about 600 RPM.

Production of the narasin antibiotic can be monitored during the fermentation by either agar diffusion or turbidimetric methods. Test organisms suitable for use include *Staphylococcus aureus*, *Bacillus subtilis*, and *Micrococcus luteus*.

Antibiotic activity is generally present after about 40 hours and remains present for at least 2 or more days during the fermentation period. Peak antibiotic production occurs from about 2 to about 4 days fermentation time.

The narasin antibiotic can be recovered from the fermentation medium by methods known in the art and described by Berg et al. in U.S. Pat. No. 4,038,384.

The novel narasin-producing organism *Streptomyces lydicus* DeBoer et al, NRRL 12034 produces good amounts of narasin factor A, as well as slight amounts of narasin factor D. The components may, as desired, be obtained as single antibiotics by further purification of the complex, for example by column chromatographic techniques. These are described in U.S. Pat. No. 4,038,384, which disclosure is hereby incorporated into and made a part of this application.

In order to illustrate more fully the operation of this invention, using varying fermentation media, the following Examples are provided. However, the scope of the invention is not intended to be limited thereby.

EXAMPLES

EXAMPLE 1

A medium was prepared for use in the agar slant culture of *Streptomyces lydicus* DeBoer et al., NRRL 12034:

| Ingredient | Amount (g/L.) |
| --- | --- |
| Potato dextrin | 10.0 |
| Enzyme-hydrolyzed casein[1] | 2.0 |
| Beef extract | 1.0 |
| Yeast extract | 1.0 |
| Agar | 2.0 |
| Czapek's mineral stock | 2.0 ml/L. |
| Deionized water | q.s. to 1.0 liter |

[1]N-Z-Amine A (Humko Sheffield Chemical Co., Memphis, Tenn.)

Czapek's mineral stock is prepared from the following ingredients:

| Ingredient | Amount (g/100 ml) |
| --- | --- |
| KCl | 10.0 |
| $MgSO_4 \cdot 7H_2O$ | 10.0 |
| $FeSO_4 \cdot 7H_2O$ | 0.2 |
| Deionized water | q.s. to 100 ml. |

Spores of *Streptomyces lydicus* DeBoer et al., NRRL 12034, were inoculated on a nutrient agar slant made up of the above-identified ingredients, and the thus-inoculated slant was incubated for about 7 days at a temperature of about 30° C. The mature slant culture was then covered with water and scraped with a sterile tool to loosen the spores and mycelium. One milliter of the resulting spore suspension was used to inoculate 50 ml. of vegetative medium of the following composition:

| Ingredient | Amount (g/L.) |
| --- | --- |
| Dextrose | 15.0 |
| Soybean meal | 15.0 |
| Corn steep liquor | 5.0 |
| $CaCO_3$ | 2.0 |
| NaCl | 5.0 |
| Czapek's mineral stock | 2.0 ml/L. |
| Deionzed water | q.s. to 1.0 liter |

The vegetative inoculum was incubated in a 250 ml. wide-mouth Erlenmeyer flask at about 30° C. for about 48 hours on a shaker rotating through an arc two inches in diameter at 250 RPM. This incubated medium is used either to inoculate small fermentors (the inoculum being approximately 1% per volume of medium) or to inoculate second stage flasks for the production of a larger volume of mycelium.

Two hundred milliter aliquots of the production medium were placed in 1.0 liter Erlenmeyer flasks and were sterilized at 121° C. for about 30 minutes. When cooled the flasks were inoculated with a 5% inoculum of the vegetative inoculum. The culture was incubated on a reciprocal shaker at 108 SPM with a two-inch stroke. The pH of the fermentation at the end of 72 hours was about 8.0. The fermentation was run at 30° L C.

EXAMPLE 2

Narasin was produced using a sterile production medium having the following composition:

| Ingredient | Amount (g/L.) |
| --- | --- |
| Silicone antifoam agent[1] | 0.2 |
| Glucose | 10.0 |
| Molasses | 20.0 |
| Peptone | 5.0 |
| $CaCO_3$ | 2.0 |
| Deionized water | q.s. to 9.0 liters |

[1]Dow-Corning Antifoam A

This production medium, having a pH of 6.7, was inoculated with 2.0% inoculum from the second-stage medium obtained as described in Example 1. The inoculated production medium was allowed to ferment in a 10-liter fermentation tank for about 3 days at a temperature of about 30° C. The fermentation medium was aerated with sterile air at the rate of 0.5 v/v/m and was stirred with conventional agitators at about 400 RPM.

EXAMPLE 3

Narasin was produced according to the procedure of Example 2, but using a sterile production medium having the following composition:

| Ingredient | Amount (g/L) |
| --- | --- |
| Silicone antifoam agent[1] | 0.2 |
| Glucose | 25.0 |
| Corn starch | 10.0 |
| Liquid meat peptone | 10.0 |
| Enzyme-hydrolyzed casein[2] | 4.0 |
| Molasses, Blackstrap | 5.0 |
| $MgSO_4 \cdot 7H_2O$ | 0.5 |
| $CaCO_3$ | 2.0 |
| Czapek's mineral stock | 2.0 ml. |
| Deionized water | q.s. to 9.0 liters |

[1]Dow-Corning Antifoam A
[2]N-Z-Amine A (Humko Sheffield Chemical Co., Memphis, Tenn.)

This production medium, having a pH of 6.5, was inoculated with 2.0% inoculum and was allowed to ferment in a 10-liter fermentation tank for about 4 days at a temperature of about 30° C. The fermentation medium was aerated with sterile air at the rate of 0.5 v/v/m and was stirred with a conventional agitator at about 600 RPM.

EXAMPLE 4

Narasin was produced according to the procedure of Example 2, but using a sterile production medium having the following composition:

| Ingredient | Amount (g/L.) |
| --- | --- |
| Silicone antifoam agent[1] | 0.2 |
| Tapioca dextrin | 30.0 |
| Enzyme-hydrolyzed casein[2] | 10.0 |
| Czapek's mineral stock | 2.0 ml. |
| Deionized water | q.s. to 9 liters |

[1]Dow-Corning Antifoam A
[2]N-Z-Amine A (Humko Sheffield Chemical Co., Memphis, Tenn.)

This production medium, having a pH of 6.4, was adjusted to pH 7.1 with approximately 3 ml. of 10 N aqueous potassium hydroxide before sterilization, and was then inoculated with 2% inoculum. The medium was allowed to ferment in a 10-liter fermentation tank for about 3 days at a temperature of about 30° C. The fermentation medium was aerated with sterile air at the rate of 0.5 v/v/m and was stirred with a conventional agitator at about 600 RPM.

EXAMPLE B 5

Isolation and Purification

Ten liters of fermentation broth was filtered using filter aid (Hyflo Supercel filter air, a diatomaceous earth produced by Johns-Manville Corp.), and the filter cake was washed with water. The broth filtrate was combined with the water wash and extracted two times with 4.5 L. portions of ethyl acetate. The ethyl acetate extracts were combined and concentrated in vacuo to yield an oily residue. The residue was dissolved in 100 ml. of acetone, and 100 ml. of water was added. The pH of the solution was adjusted to pH 3.0 with 1 N aqueous hydrochloric acid, and the solution was stirred for about 1 hour at room temperature. The crystals which formed were filtered off and washed with cold water. The crystals were recrystallized by dissolving them in 50 ml. of acetone, adding 50 ml. of water, and allowing the mixture to stand overnight at room temperature. The crystals which formed were filtered off, washed with cold water, and dried in vacuo to yield 100 mg. of white crystals. The crystals were shown to be identical to narasin by NMR, IR, UV, and mass spectra, and by thin layer chromatography-bioautography.

I claim:

1. The method of producing the antibiotic narasin which comprises cultivating *Streptomyces lydicus* DeBoer et al., NRRL 12034, or a narasin-producing mutant or variant thereof, in a culture medium containing assimilable sources of carbohydrate, nitrogen, and inorganic salts under submerged aerobic fermentation conditions until a substantial amount of antibiotic activity is produced by said organism in said culture medium.

2. The method of claim 1 wherein the organism is *Streptomyces lydicus* DeBoer et al., NRRL 12034.

3. The method of claims 1 or 2 which includes the additional step of separating narasin from the culture medium.

4. A biologically pure culture of the microorganism *Streptomyces lydicus* DeBoer et al., NRRL 12034, which is capable of producing narasin in a recoverable quantity upon cultivation in a culture medium containing assimilable sources of carbohydrate, nitrogen, and inorganic salts under submerged aerobic fermentation conditions.

* * * * *